United States Patent
Ellenbogen et al.

(10) Patent No.: US 7,016,459 B2
(45) Date of Patent: Mar. 21, 2006

(54) FOLDED ARRAY CT BAGGAGE SCANNER

(75) Inventors: Michael Ellenbogen, Wayland, MA (US); Richard Robehr Bijjani, North Chelmsford, MA (US)

(73) Assignee: L-3 Communications Security and Detection Systems, Inc., Woburn, MA (US)

( * ) Notice: Subject to any disclaimer, the term of this patent is extended or adjusted under 35 U.S.C. 154(b) by 16 days.

(21) Appl. No.: 10/972,211

(22) Filed: Oct. 21, 2004

(65) Prior Publication Data

US 2005/0169423 A1    Aug. 4, 2005

Related U.S. Application Data

(63) Continuation of application No. 10/677,976, filed on Oct. 2, 2003.

(60) Provisional application No. 60/415,391, filed on Oct. 2, 2002.

(51) Int. Cl.
*G01N 23/00* (2006.01)
(52) U.S. Cl. .......................... 378/19; 378/57
(58) Field of Classification Search .................. 378/57, 378/58, 4–20
See application file for complete search history.

(56) References Cited

U.S. PATENT DOCUMENTS

| | | | |
|---|---|---|---|
| 4,029,963 A * | 6/1977 | Alvarez et al. ............. | 378/5 |
| 4,070,581 A | 1/1978 | Gibbons et al. | |
| 4,075,492 A | 2/1978 | Boyd et al. | |
| 4,138,721 A | 2/1979 | Boyd | |
| 4,149,078 A | 4/1979 | Hahn et al. | |
| 4,247,774 A | 1/1981 | Brooks | |
| 4,266,136 A | 5/1981 | Duinker | |
| 4,298,799 A | 11/1981 | Oliver | |
| 4,315,157 A | 2/1982 | Barnes | |
| 4,599,740 A * | 7/1986 | Cable ........................... | 378/57 |
| 4,756,015 A | 7/1988 | Doenges et al. | |
| 4,759,047 A | 7/1988 | Donges et al. | |
| 4,783,794 A | 11/1988 | Dietrich | |
| 4,796,183 A * | 1/1989 | Ermert et al. ................. | 378/10 |
| 4,817,121 A | 3/1989 | Shimizu et al. | |
| 4,841,554 A | 6/1989 | Doenges et al. | |
| 4,870,670 A | 9/1989 | Geus | |
| 5,164,973 A | 11/1992 | Takahashi et al. | |
| 5,367,552 A | 11/1994 | Peschmann | |
| 5,570,403 A | 10/1996 | Yamazaki et al. | |
| 5,583,903 A | 12/1996 | Saito et al. | |
| 5,661,774 A | 8/1997 | Gordon et al. | |

(Continued)

FOREIGN PATENT DOCUMENTS

EP    0 471 455 A2    2/1992

(Continued)

OTHER PUBLICATIONS

U.S. Appl. No. 10/971,453, filed Oct. 21, 2001, Ellenbogen.

(Continued)

*Primary Examiner*—Craig E. Church
*Assistant Examiner*—Jurie Yun
(74) *Attorney, Agent, or Firm*—Wolf, Greenfield & Sacks, P.C.

(57) ABSTRACT

A reduced size CT scanner for baggage inspection has a wide angle x-ray source and multiple sets of detectors at different distances from the x-ray source. The detectors in each set are sized and positioned to maintain consistent pitch and flux levels among all detectors. Conventional reconstruction processes can be used to process the data from the CT scanner. The scanner may also be incorporated into a check-in desk in a network of scanners.

5 Claims, 10 Drawing Sheets

U.S. PATENT DOCUMENTS

| | | | |
|---|---|---|---|
| 5,692,029 | A | 11/1997 | Husseiny et al. |
| 5,848,117 | A | 12/1998 | Urchuk et al. |
| 5,867,553 | A | 2/1999 | Gordon et al. |
| 5,912,938 | A | 6/1999 | Dobbs et al. |
| 5,917,876 | A | 6/1999 | Fujii et al. |
| 6,018,562 | A | 1/2000 | Willson |
| 6,185,272 | B1 | 2/2001 | Hiraoglu et al. |
| 6,218,943 | B1 | 4/2001 | Ellenbogen |
| 6,301,326 | B1 | 10/2001 | Bjorkholm |
| 6,335,957 | B1 * | 1/2002 | DiBianca ..................... 378/19 |
| 6,647,091 | B1 * | 11/2003 | Fenkart et al. ................ 378/57 |
| 6,658,082 | B1 * | 12/2003 | Okumura et al. ............ 378/19 |
| 2004/0120454 | A1 | 6/2004 | Ellenbogen et al. |

FOREIGN PATENT DOCUMENTS

| | | |
|---|---|---|
| EP | 0 816 873 A1 | 1/1998 |
| EP | 0 825 457 A1 | 2/1998 |
| WO | WO 97/18462 | 5/1997 |
| WO | WO 03/065077 A2 | 8/2003 |
| WO | WO 2004031755 A2 | 4/2004 |
| WO | WO 2004031755 A3 | 4/2004 |

OTHER PUBLICATIONS

Affidavit of James Buckley in Opposition to Plaintiff's Patent Motions, Redacted Version, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).

Affidavit of Richard Biijani in Opposition to Plaintiff's Patent motions, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).

Affidavit of A. W. Phinney in Opposition to Plaintiff's Emergency Motion Regarding "Newly Found Evidence", Redacted Version, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).

Affidavit of Elan Scheinman in Opposition to Plaintiff's Patent Motions, Redacted Version, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).

Affidavit of A. W. Phinney in Opposition to Plaintiff's Patent Motions, Redacted Version, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).

Affidavit of Michael Ellenbogen in Opposition to Plaintiff's Emergency Motion, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).

Affidavit of Michael Ellenbogen in Opposition to Plaintiff's Patent Motions, Redacted Version, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).

Plaintiff's Amended Verified Complaint dated May 18, 2004 in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS1 (Justice van Gestel).

Defendant's Answer dated May 24, 2004 in a case entitled *L-3 Communications Security and Detection Systems Corporation Delaware* v. *Reveal Imaging Technologies, Inc.* Commonwealth of Massachusetts, Superior Court Department (BLS) of the Trial Court, Civil No. 03-05810-BLS1 (Justice van Gestel).

The Court's "Memorandum and Orders on Various Motions and Related Matters" dated Dec. 2, 2004, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS1 (Justice van Gestel).

Decision On Petition in *In re Ellenbogen, et al.*

International Search Report for PCT/US2003/31718, mailed Jun. 11, 2004.

International Search Report for PCT/US2004/001929, mailed Jul. 14, 2004.

Eilbert and Krug, "Aspects of Image Recognition in Vivid Technology's Dual-energy X-ray System for Explosive Detection," Proceedings of the International Society for Optical Engineering, vol. 1824, Nov. 1992.

Documents bearing production Nos. REVL 05746 to REVL 05761 produced by the defendant in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).

Nick Fox, "X-ray Screening Uncovered" Airport Safety Security Service, vol. 5, Oct. 2004.

InVision Technologies, "Technical Specifications" for CTX9000 DSI.

L-3 Communications, literature for eXaminer 3DX6000, http://www.dsxray.com/Linescan.asp?ProductCode=eXaminer6, Aug. 2, 2004, pp. 1-3.

Analogic product literature, "The Exact: An Advanced Explosive Detection System,".

Federal Register, "Part IX, Department of Transportation," Federal Aviation Admin., Explosives Detection Systems; Notices, Monday Apr. 13, 1998.

L-3 Communications Security and Detection Systems, Inc., VividCT Series, www/bombdetection.com; Rev. Oct. 2002.

Rapiscan X-ray System Maintenance Manual 1995.

Terry Peters, "CT Image Reconstruction," SLIDES REVL 05697-05745, pp. 1-49.

Michael D. Silver, "High-helical-pitch, cone-beam computed tomography," Phys. Med. Biol., 43 (1998) 847-855, REVL 05688-05696.

Dan Kedem, et al, "Computed Tomography for Thick Steel Pipes and Castings," Electric Power Research Inst., Dec. 1986, REVL 05565-05682.

U.S. Army Medical Research Acquisition Activity, Contract DAMD17-87-C-7108, Dated Jun. 1, 1987; REVL 05479-05487.

Berthold K.P. Horn, "Fan-Beam Reconstruction Methods," A.I. Memo No. 448, Nov. 1977 REVL 05425-05469.

Patrick Michael, et al, "The Architecture of Secure Flow," REVL 05288-05295.

Tim Rayner et al., "Threat Vector Solutions," REVL 05283-05287.

Heimann, Check-In Counter X-Ray System CS 5070, REVL 4936-4941.

MUX Training, Apr. '03, with CTX9000 DSI Product Announcement, REVL 4926-4932.

InVision Technologies, "A Clear Vision, A Vital Mission," REVL 4933-4935.

Jim Aldo et al., "Enhanced Integration, Data Fusion and Communication Protocols for Integrated Checked Baggage Explosives Detection Screening," Nov. 1996, pp. 385-390, REVL 4909-4913.

Dr. Wagih Hassan Makky, "Proceedings of the Second, Explosives Detection Technology Symposium & Aviation Security Technology Conference," REVL 4781-4788.

David S. de Moulpied et al., Security Management, Mar. 1992, REVL 4855-4898.

InVision Technologies, "A Clear Vision, A Vital Mission," REVL 4778-4780.

InVision Technologies, Product Announcement, Multiplexing for the CTX 9000 DSi, REVL 4772-4777.

"Proceedings, IEEE Dec. 1979, Collecting Data with Fan Beams," REVL 4759-4767.

KSI Kaiser System Inc., OmniBlock X-Ray Source, REVL 4768-4769-.

Invision Technologies, Image Archiving, REVL 4897-4898.

Slide entitled L-Shaped Array (Conventional X-Ray Technology).

The Reveal Parties' Opposition to Plaintiff's Emergency Motion Regarding "Newly Found Evidence" in a case entitled *L-3 Communications Security and Detection Systems Corporation Delaware v. Reveal Imaging Technologies, Inc.*, Commonwealth of Massachusetts, Superior Court Department (BLS) of the Trial COurt, Civil No. 03-05810-BLS (Justice van Gestel).

Deposition of David A. Schafer dated Thursday, May 12, 2005, in a case entitled *L-3 Communications Security and Detection Systems Corporation v. Reveal Imaging Technologies, Inc.*, Commonwealth of Massachusetts, Superior Court Department (BLS) of the Trial Court, Civil No. 03-05810-BLS (Justice van Gestel). including exhibits 1, 6, 7, 10-19.

* cited by examiner

FOLDED ARRAY CT BAGGAGE SCANNER

CROSS REFERENCE TO RELATED APPLICATIONS

This application is a continuation of U.S. patent application Ser. No. 10/677,976 entitled "FOLDED ARRAY CT BAGGAGE SCANNER," filed Oct. 2, 2003, which claims the benefit, under 35 U.S.C. §119(e), of the filing date of U.S. Provisional Application Ser. No. 60/415,391 entitled "BAGGAGE INSPECTION SYSTEM," filed Oct. 2, 2002.

BACKGROUND OF THE INVENTION

1. Field of the Invention

The present invention relates to a Computed Tomography (CT) system for inspecting baggage for explosives or other contraband. More particularly, it relates to a novel Computed Tomography (CT) scanner design having a reduced size.

2. Discussion of Related Art

Following the terrorist attacks on Sep. 11, 2001, the United States government decided to implement additional airport security. One of the security measures which were to be implemented was inspection of all checked baggage for explosives. In November 2001, Congress passed the Aviation and Transportation Security Act, which mandated 100% explosive detection screening of checked baggage by Dec. 31, 2002. It was expected that the screening requirements would be met through a combination of Explosive Detection Systems (EDS) and Explosive Trace Detection systems (ETD). EDS is faster, but more expensive and more prone to false alarms. ETD is much slower, more invasive and requires more manual input. Congress later extended the deadline for full deployment until Dec. 21, 2003, on a case by case basis, as long as approved interim methods, such as canine teams, hand searches and passenger bag matching, were employed.

Implementation of this security measure using existing technology has been and will continue to be cumbersome and expensive. Even by the end of 2003, the implemented solutions are unlikely to be permanent solutions. In many cases, airports have deployed hand-fed machines in terminal lobbies, usurping premium space, or implemented the manpower-intensive ETD systems. In order to improve efficiency, reduce manpower requirements, and recover lobby space, airports will transition to EDS machines integrated into airport baggage handling system. However, existing EDS machines are not easily deployed or integrated into existing baggage handling systems.

Known Explosives Detection Systems (EDS) utilize either Computed Tomography (CT) technology, or a combination of x-ray and CT technology, to create an image of the contents of a bag. Projection x-ray systems have been used for many years with carry-on baggage. However, such systems require operator review of all images and provide slow throughput. Furthermore, these systems also cannot provide thickness or density information for objects in order to provide explosive detection.

A Computed Tomography (CT machine has been designed to perform automated explosives detection for passenger baggage, parcels, mail, and small cargo prior to loading onto an aircraft. CT technology has been proven to successfully meet the US TSA Certification requirements for automated explosives detection (EDS) in airline checked baggage. While CT technology is effective for explosive detection, use of existing CT technology in checked baggage inspection has many drawbacks. CT machines incorporate a rotating ring or "gantry" on which the X-ray source and detectors are mounted. FIG. 1 is a cross sectional view of a conventional CT scanner 10. The CT scanner 10 includes a gantry 11 surrounding a tunnel 20. A conveyor (not shown) moves baggage through the tunnel 20 for scanning. The gantry 11 rotates about the tunnel, producing one slice of data for each rotation. An x-ray source 30 produces a narrow angle beam 40. A detector 31 is positioned on the gantry 11 to intersect the x-ray beam 40 passing through the tunnel. The detector 31 may consist of multiple detectors which are located equal distances from the x-ray source. The x-ray source 30 and detector 31 must be sized and positioned so that the entire region to be inspected falls within the x-ray beam. The data from the detector is analyzed using a computer to generate a cross sectional image or three-dimensional representation of the contents of the baggage being scanned.

These CT based systems have many drawbacks. They are large, heavy and require substantial space. The tunnel 20 has to be large enough to accommodate substantially all sizes of checked baggage. The x-source 30 and detector 31 must be positioned sufficiently distant from the tunnel 20 so that the entire tunnel is within the x-ray beam 40. Furthermore, the gantry 11 has to be large enough to accommodate the entire detector 31, positioned equidistant from the source. The x-ray source 30 also must be powerful enough to provide sufficient flux at the detector 31, after passing through the baggage, to overcome noise and allow for analysis. The gantry 11 also must be sturdy enough to support and balance the large x-ray source for high-speed rotation. In typical CT systems, the gantry 11 is ⅔ to 2 times the size of the tunnel 20. Furthermore, the system requires significant shielding, generally lead, to protect the operators and passengers from exposure to the powerful x-rays.

Implementation of known EDS systems for review of all baggage has proven to be difficult. In many cases, the EDS system is installed in the lobby of the airport, where it occupies a great deal of space otherwise available to passengers, retails stores, and other security processes. The large weight of the system often requires strengthened lobby floors. Alternatively, as has been done in some airports, the EDS system could be integrated into the baggage conveyor system which transfers the baggage from the lobby to the loading area. However, such systems cost millions of dollars in infrastructure modifications and disruption of airport operations to install. Also, the conveyors through the CT system must move at a slow speed to generate sufficient data for reconstruction of the contents of the baggage from the slices. In order to accommodate the volume of baggage at a large airport, a substantial number of scanners are required. With multiple scanners, coordination of operation issues arise.

SUMMARY OF THE INVENTION

The deficiencies of the prior art are substantially overcome by the CT scanner of the present invention which includes a wide angle x-ray tube and multiple sets of detectors. One set of detectors is centered on the x-ray source with one or more additional sets covering outer edges of the wide angle x-ray beam. The CT scanner of the present invention has a reduced size while maintaining the same tunnel size as conventional scanners. According to another aspect of the invention, the sets of detectors have different pitches in order to maintain a constant inter-detector angle. Thus, reconstruction algorithms can be simplified. According to another aspect of the invention, detectors are positioned on only half of the detector ring. According to another aspect of the invention, a second set of detectors sensitive to a different energy spectrum are positioned on the other half of the detector ring. The CT scanner of the present invention can provide dual energy analysis from a single scan of a bag, using the multiple sets of detectors.

According to another aspect of the invention, the x-ray source operates at a reduced flux level from conventional systems. Due to the compact size of the CT scanner of the invention, the shorter distances from the source to the detector allows for a less powerful x-ray. According to another aspect of the invention, a portion of a bag can be scanned multiple times with the results being averaged. The data from the multiple scans is averaged to remove noise. The resulting reduction in noise allows a reconstruction of heavy bags with a reduced flux x-ray source.

According to another aspect of the invention, the reduced size CT scanner is incorporated into an airline check-in desk. The CT scanner is positioned to allow the passenger to insert the bag to be checked. Upon successful scanning and analysis (or prior to scanning and analysis), the baggage is tagged by airline personnel in the regular manner and transferred to the existing baggage handling system. According to another aspect of the invention, a plurality of CT scanners are networked

DETAILED DESCRIPTION

Figure 1:
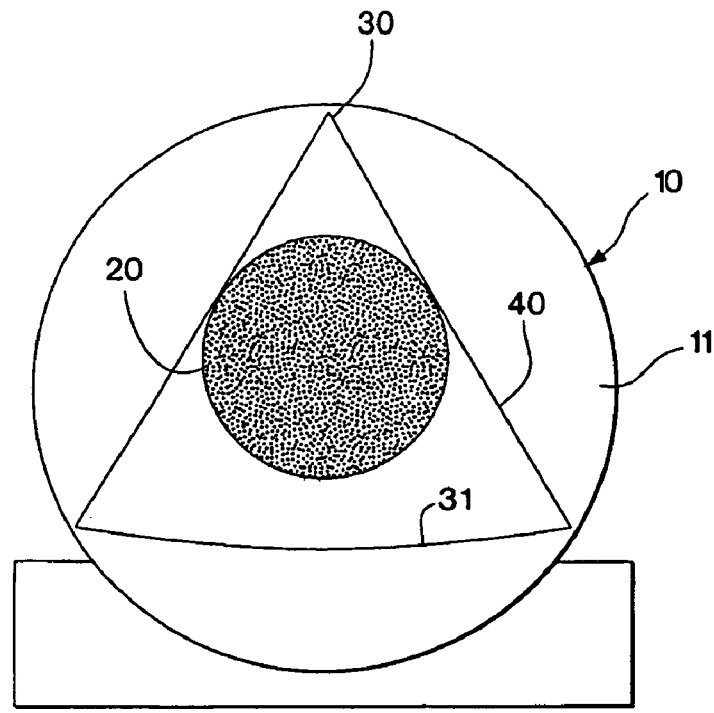
FIG. 1 is a cross sectional view of a conventional CT scanner.
Figure 2:
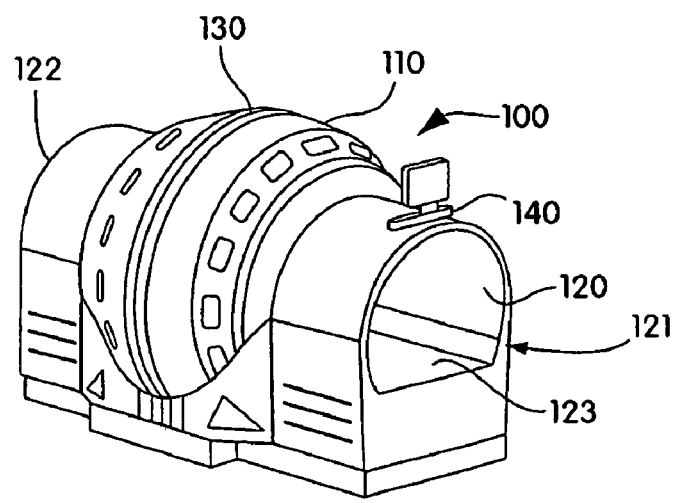
FIG. 2 is a perspective view of a CT scanner according to an embodiment of the present invention.

A CT scanner of the present invention has a more compact size than conventional scanners through the use of a wide angle x-ray source and a folded detector array, including sets of detector arrays at different distances from the x-ray source. FIG. 2 illustrates an embodiment of a CT scanner 100 according to an embodiment of the present invention. The CT scanner 100 includes a housing 110 with a substantially circular tunnel 120, there through. The tunnel 120 has an input end 121 and an output end 122. A conveyor 123 extends from the input end 121 to the output end 122 of the tunnel 120. For ease loading baggage, the conveyor may extend beyond the ends of the tunnel 120. Additionally, other conveyors may be positioned and used to transfer baggage to or from the conveyor 123 in the CT scanner 100. Coverings (not shown), such as lead lined rubber or fabric, may be placed within the tunnel 120 or at the input end 121 and output end 122, to provide x-ray shielding. The CT scanner 100 has a x-ray area 130 towards its center. As illustrated in FIG. 2, the x-ray area 130 may be larger than the ends 121, 122 of the tunnel 130. Alternatively, the housing 110 could be formed of a single size to accommodate the size of the x-ray area 130.

Figure 3A:
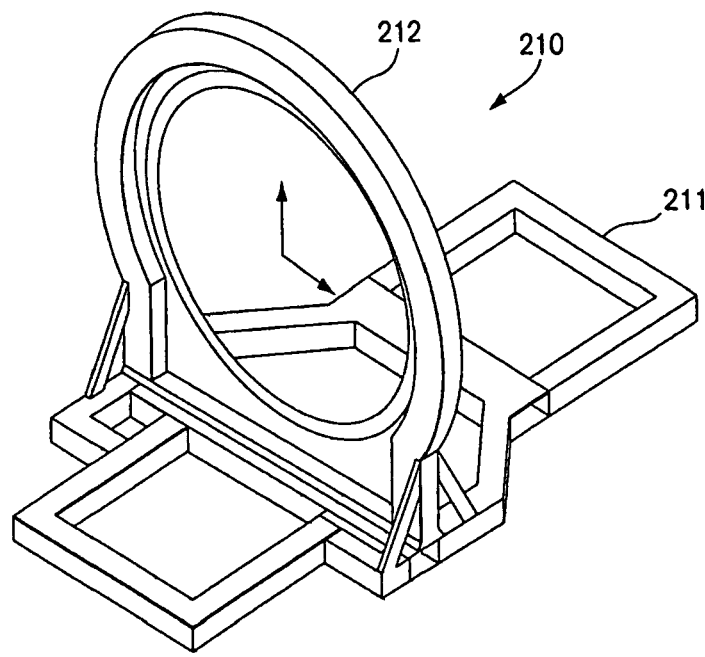
FIGS. 3A and 3B are perspective views of a gantry system according to an embodiment of the present invention.
Figure 3B:
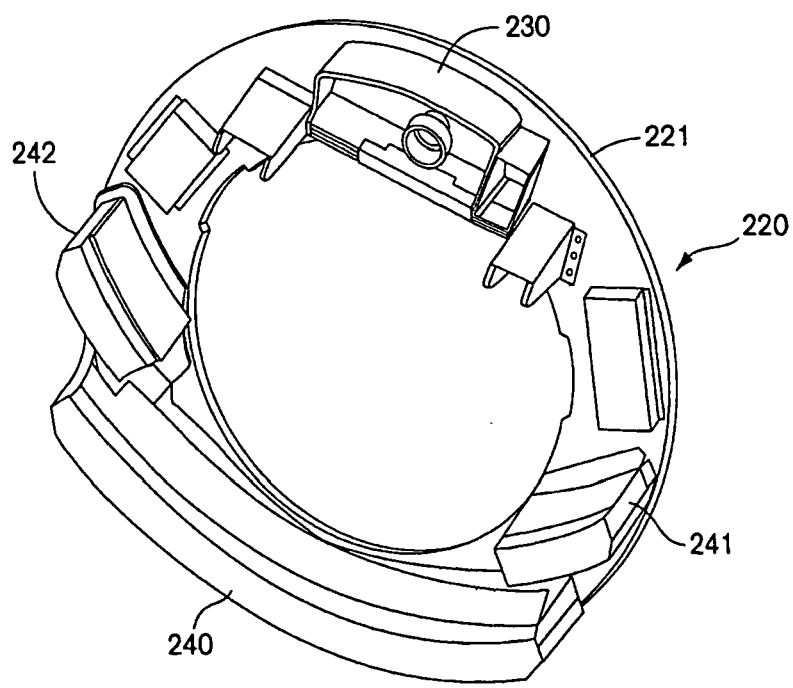

FIGS. 3A and 3B illustrate a gantry system disposed within the x-ray area 130 of the housing 110. The gantry system includes a support structure 210 (FIG. 3A) and a gantry 220 (FIG. 3B). The support structure 210 includes a base 211 and a circular shaped vertical support 212. The vertical support 212 is attached to the base 211. The gantry 220 includes a ring 221 which is rotatably attached to the vertical support 212 so that the tunnel 120 passes through the center of the ring 221. An x-ray source 230 is attached to the ring 221 to provide a wide angle x-ray beam over the entire area of the tunnel 120. Preferably, the x-ray source has a rounded shape on an upper surface, similar in shape to the outer surface of the gantry. In this manner, the size of the gantry can be reduced since it does not need to accommodate the extensions of a rectangular x-ray source. Furthermore, the gantry has a three sets of detector arrays 240, 241, 242, positioned on the ring 221 within the projected beam of the x-ray source 230. Notably absent from the gantry is a computer. Conventional CT scanners include a computer on the gantry to process data from the detectors and format the data for transmission from the gantry to a host computer which operates the scanner. According to an embodiment of the present invention, the CT scanner does not include a computer on the gantry. Instead, data from the detectors are streamed directly to the host computer. Elimination of the computer on the gantry permits a smaller and lighter gantry. As with conventional CT scanners, the gantry includes an edge contact (not shown) for transferring power and control signals to the gantry and data from the gantry while the gantry is rotating. Of course, the present invention may include a computer on the gantry to perform some of the processing of data as in conventional CT scanners.

Figure 4:
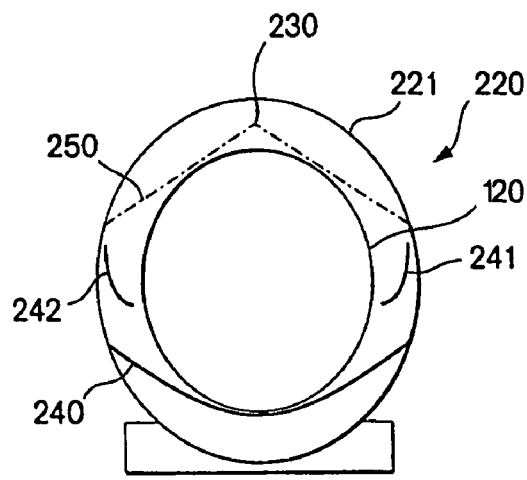
FIG. 4 is a cross sectional illustration of a CT scanner gantry according to an embodiment of the present invention.

FIG. 4 illustrates the positioning of the x-ray source 230 and the folded array detectors 240, 241, 242 on the ring 221. The ring 221 of the gantry 220 is substantially smaller than for conventional CT scanners with a similar size tunnel 120. According to an embodiment of the present invention, the gantry has a diameter of approximately 130 cm, when the tunnel is approximately 80 cm in diameter. A conventional CT scanner with a 80 cm diameter tunnel would be approximately 210 centimeters. Thus, with the present invention, the CT scanner is reduced in size by approximately 40%. The wide angle x-ray source 230 is located on the gantry 220 so that the x-ray beam intersects the entire area of the tunnel 120. Since the x-ray source 230 has a wider beam 250 than for a conventional CT scanner, it can be positioned closer to the tunnel. The CT scanner of the present invention includes a folded detector array including two or more sets of detectors 240, 241, 242 at different distances from the x-ray source 230. One set of detectors 240 covers a central portion of the gantry ring and is centered on the x-ray source at a distance equal to the source to center detector distance. The other sets of detectors 241, 242 are positioned to intersect the outer ranges of the x-ray fan beam 250. According to an embodiment of the invention, the second sets of detectors 241, 242 start at the point in the beam 250 where the inner detectors 240 reach the edge of the ring 221. Alternatively, the second set of detectors may start at any location in the beam 250 where the inner detectors end, depending upon the size of the machine and the gantry. The second set of detectors 241, 242 are a closer distance to the x-ray source 230 than the inner detectors 240.

Figure 12:
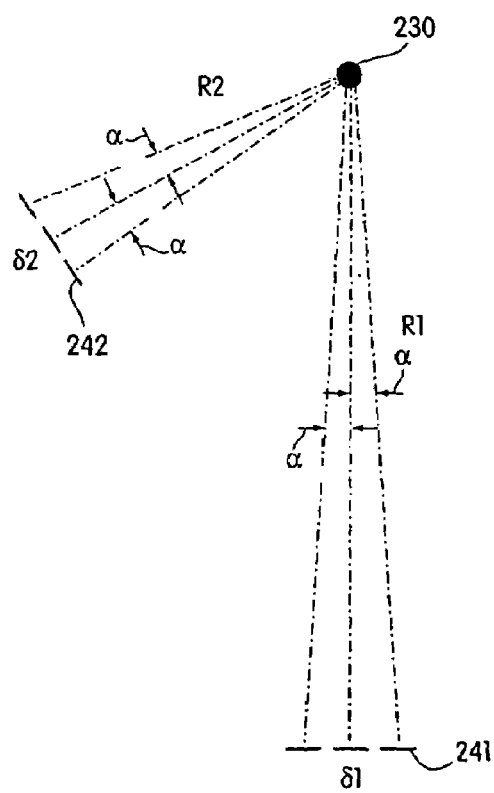
FIG. 12 represents the pitch between detector elements according to an embodiment of the invention.

Since the detectors are closer to the x-ray source, they can have a shorter pitch than for conventional CT scanners without sacrificing flux levels or photon counts. According to an embodiment of the present invention, the detector elements are sized and positioned so that each set of detectors has substantially identical pitch and flux levels. The closer distance between the x-ray source 230 and the second sets of detectors 241, 242 allows a smaller detector pitch than for the first set of detectors 240. Since the distance is shorter, the photon count per unit area at the second sets of detectors 241, 242 is higher than for the first set of detectors 240. The higher photon count allows a reduced detector pitch without sacrificing the signal to noise ratio. Additionally, with the reduced pitch, a constant inter-detector angle can be maintained throughout the fan beam 250. FIG. 12 illustrates the relationship between the first set of detectors 240 and the second sets of detectors 241, 242. The angles between detectors ($\alpha$) remains constant while the pitch between detectors ($\delta 1$, $\delta 2$) changes. To maintain the same angle, the equation $\delta 1/R1=\delta 2/R2$ must be satisfied. Additionally, to maintain a minimum flux level, the following equation, $(\delta 2 \times w2)/R2^2 > (\delta 1 \times w1)/R1^2$, where w1 and w2 are the widths of the detectors, must be satisfied. Since the distance is reduced, both equations can be satisfied, with consistent angles and minimal noise interference. These features allow for simplified reconstruction software. Known 'equi-angular' fan beam reconstruction algorithms can be used with minimal modification. According to an embodiment of the invention, the detector elements of the first set of detectors 240 are approximately 10 mm long and 2.2 mm wide. The detector elements of the second sets of detectors 241, 242 are 8 mm long and 1.8 mm wide.

Figure 5:
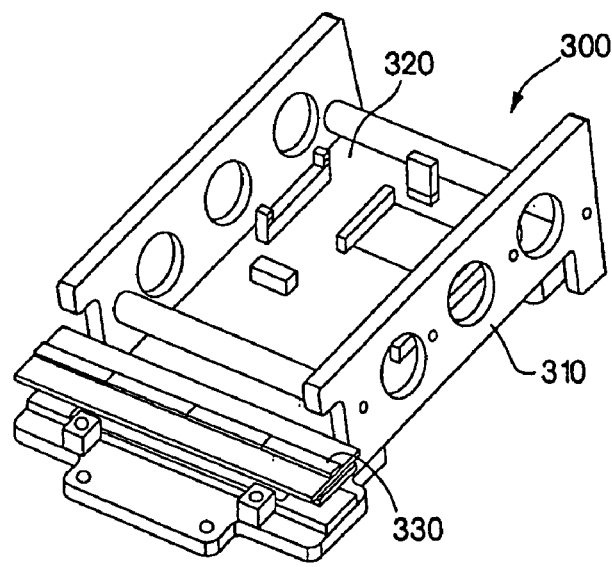
FIG. 5 is a perspective view of a detector array component of a CT scanner according to an embodiment of the present invention.
Figure 6:
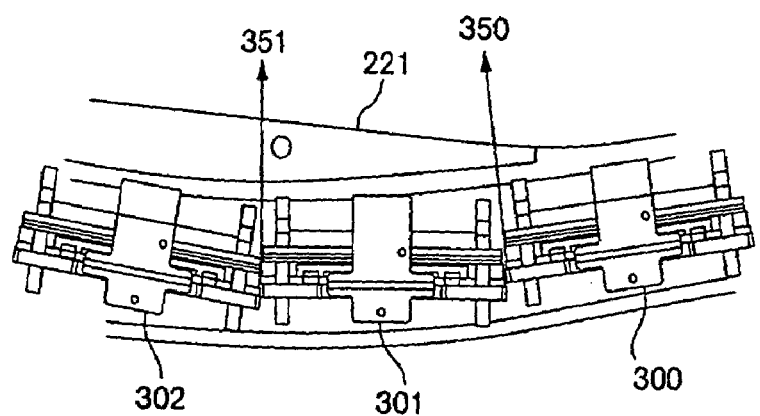
FIG. 6 is a front view of a portion of a detector of a CT scanner according to an embodiment of the present invention.

FIGS. 5 and 6 illustrate detector assemblies for simplifying the assembly of the CT scanner of the present invention and to improve quality control. FIG. 5 illustrates a detector assembly 300 having a housing 310, a processing board 320 and a detector array 330. The detector array 330 includes a plurality of detectors (not shown) arranged along the width of the assembly 300. As illustrated in FIG. 6, detector assemblies 300, 301, 302 are attached to the ring 221 of the gantry 220. The detector assemblies 300, 301, 302 are positioned so that the detector or each end of the detector array 330 is adjacent to a detector on the end of an adjacent detector array. Ideally, for purposes of reconstruction, every detector in the array would be perpendicular to and equidistant from the x-ray source. However, with flat detector assemblies 300 there are slight variations in incidence angle and distance across the assembly. According to an embodiment of the invention, a detector assembly at the center of the first set of detectors 240 is arranged with a center detector element being perpendicular to the position of the x-ray source. For the remaining detector assemblies, the outermost detector element is perpendicular to the x-ray source. As illustrated in FIG. 6, the x-ray source direction 350, 351 is perpendicular to the left hand side of an assembly on the left hand side of the gantry. The right hand side of assemblies on the other side of the gantry would be positioned perpendicular to the direction of the x-ray source. Such positioning allows the detector arrays to be properly angled and nested, as illustrated in FIG. 6 to minimize the distance between adjacent elements on different assemblies.

The CT scanner of the present invention is smaller and less costly than conventional scanners. The wide beam width provides additional benefits in addition to reduced diameter. The shorter source to detector distances, allow for less powerful x-ray sources which translates to lower part costs, simplified cooling (quieter) and power requirements. The decrease in x-ray flux also requires less shielding, again translating to a cheaper (and lighter) system.

Figure 7:
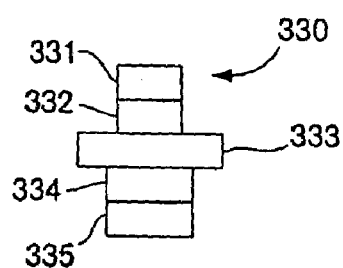
FIG. 7 is a cross sectional view of a detector component of a dual energy CT scanner according to an embodiment of the present invention.

According to an embodiment of the present invention, the CT scanner operates in a dual energy mode. FIG. 7 is a cross sectional view of a detector element 330 for dual energy operation. The detector element includes a low energy scintillator layer 331, a low energy photodiode layer 332, a copper layer 333, a high energy scintillator layer 334, and a high energy photodiode layer 335. The high energy layers 334, 335 are wider than the low energy layers 331, 332. According to an embodiment of the invention, the low energry layers are approximately 5 mm long and the high energy layers are approximately 10 mm long. The different lengths create similar flux levels between the low and high energy layers, even with the greater shielding from the copper and additional layers, thereby simplifying data acquisition electronics and subsequent signal processing. Alternatively, a dual energy scan can be performed using known techniques with a pulsing x-ray source and a single photodiode layer in the detectors.

Figure 8:
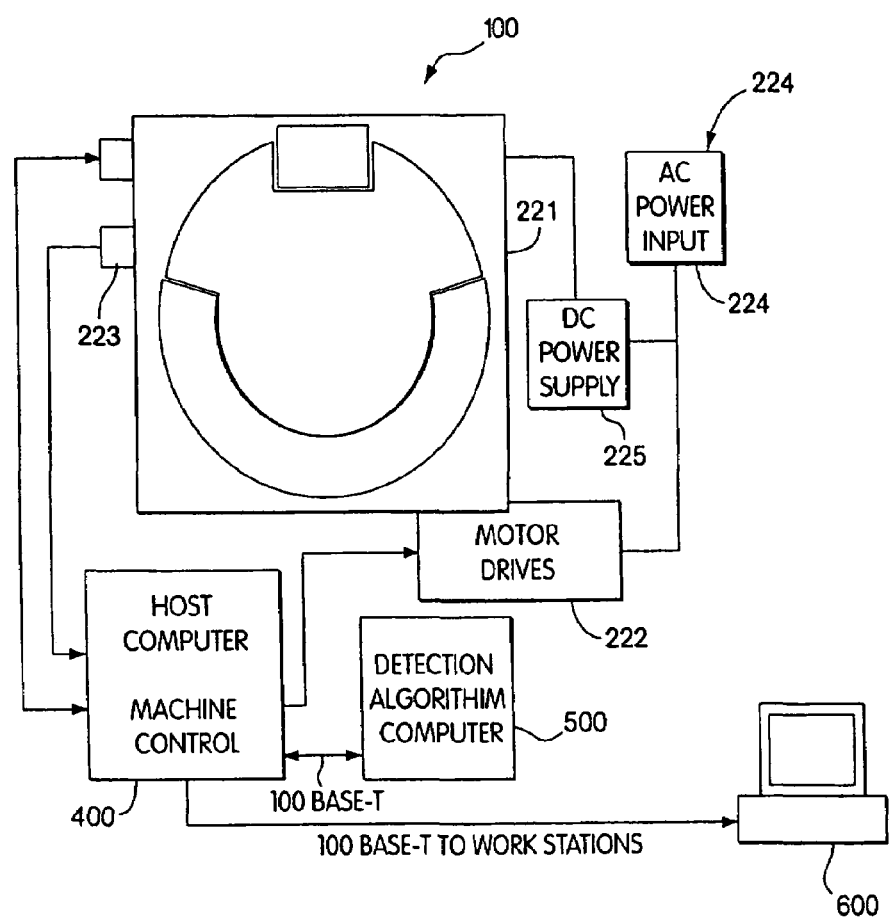
FIG. 8 is a block diagram of the components of a CT scanner according to an embodiment of the present invention.

FIG. 8 illustrates the components of a CT scanner 100 according to an embodiment of the present invention. The CT scanner 100 includes the gantry 221, and two computers 400, 500. A host computer 400 controls operation of the scanner and retrieves data from the detectors. A detection algorithm computer 500 operates on the data to determine whether an explosive device or other object of interest is present. Of course, a single computer could be used to perform all of the functions for the CT scanner. However, the use of two computers prevents the extensive processing of the detection algorithm from slowing down the operation and data collection of the CT scanner. Also, control and data elements are connected between the gantry 221 and the computers 400, 500. An AC power input 224, connected to ordinary 240 V AC power, provides the power for the CT scanner. A DC power supply 225 receives the AC power and converts it to DC power for powering the processing elements on the gantry. A set of motor drives 222, powered by the AC power, or alternatively by the DC power, operate the conveyor and rotate the gantry. A data link 223 connects the detector assemblies to the host computer 400. DC power and the data link are positioned on the ring of the gantry to provide data during rotation. The circuit boards 320 on the detector assemblies 300 sample the detectors 1440 times per second. The data is then transferred, through the data link 223 to the host computer 400. Encoders are also used to determine the rotational position of the gantry and of the conveyor. This data is also provided to the host computer.

Figure 9:
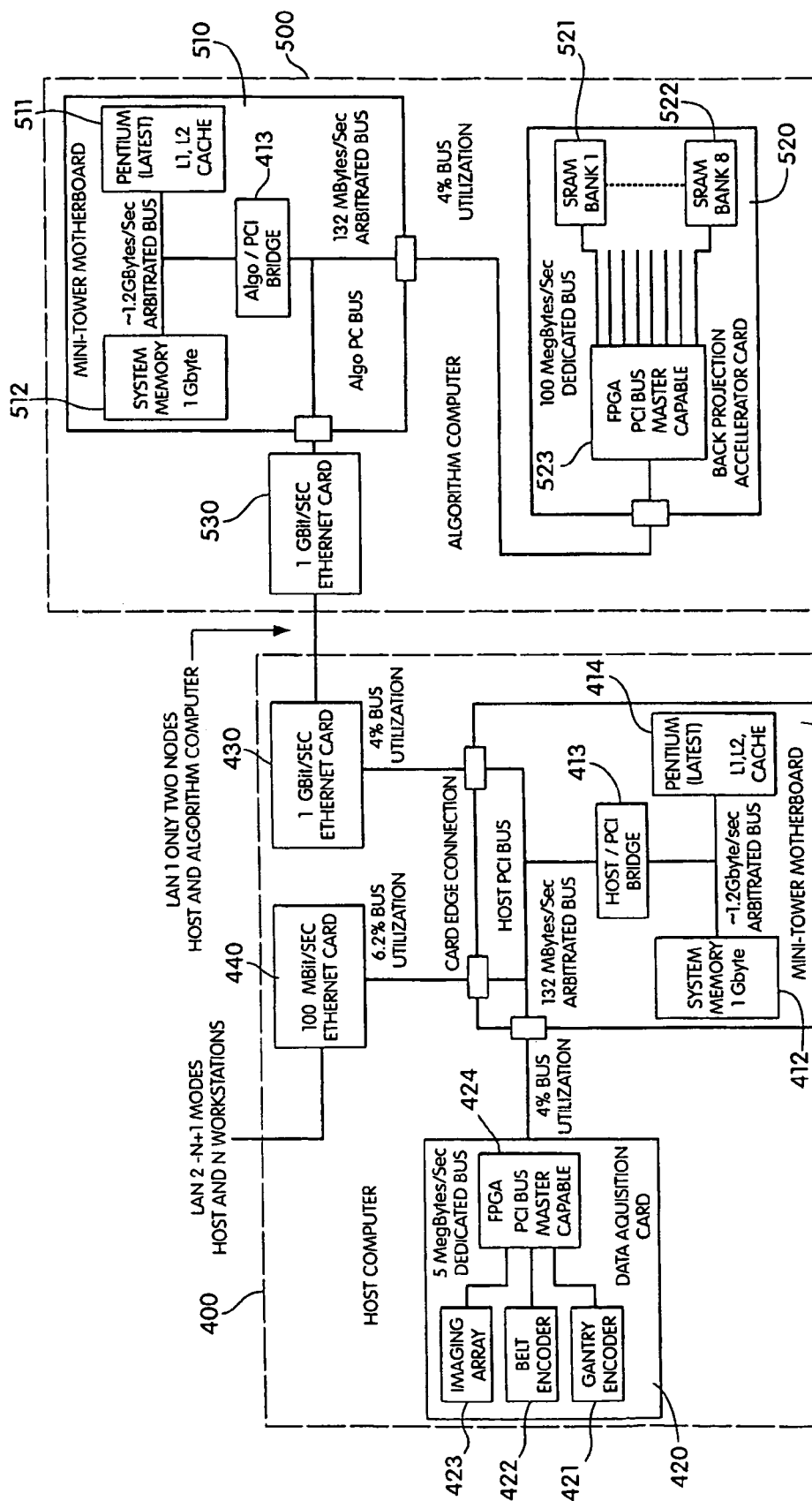
FIG. 9 is a block diagram of computer components of a CT scanner according to an embodiment of the present invention.

The components of the computers are illustrated in FIG. 9. The host computer 400 includes a motherboard 410 and a data acquisition card 420. The data acquisition card 420 includes inputs from the imaging array 423, the conveyor belt encoder 422, and the gantry encoder 421. It also includes a field programmable gate array card 424 for retrieving the data and forwarding it to the motherboard 410. The motherboard 410 includes a processor 411, such as a Pentium processor from Intel, a large RAM 412, and a back-projection accelerator card 520 for processing the data. It also includes a Host/PCI bridge for sending and receiving information from the data acquisition card and other computers. The data retrieved from the CT scanner is transferred to the detection algorithm computer 500. An ethernet connection allows quick transfer of the large amounts of data. The detection algorithm computer also includes a motherboard 510 for proper processing of the data to determine the existence of explosives or other materials.

The data from the CT scanner having a folded detector array can be processed using conventional CT operating and reconstruction techniques, such as helical scanning or start/stop scanning. The host computer is programmed to control the x-ray source, conveyor belt, and reading of detectors according to the desired scanning scheme. The detection algorithm computer, similarly, is programmed to reconstruct the CT data based upon the scanning scheme which is utilized.

Figure 10:
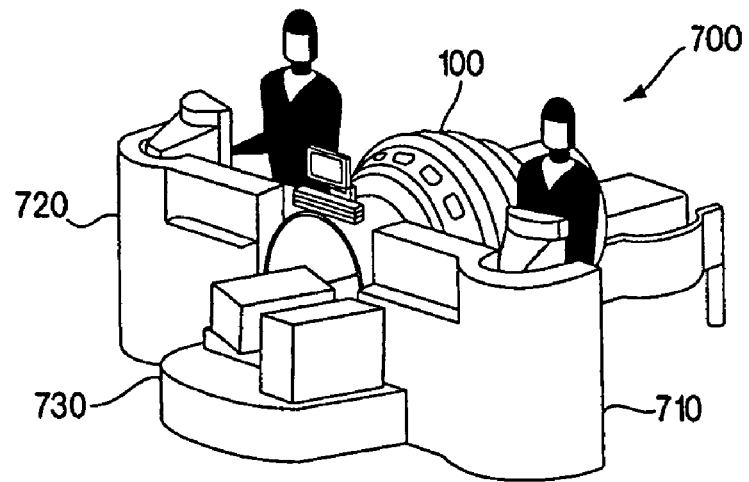
FIG. 10 is a perspective view of an airline check-in desk according to an embodiment of the present invention.
Figure 11:
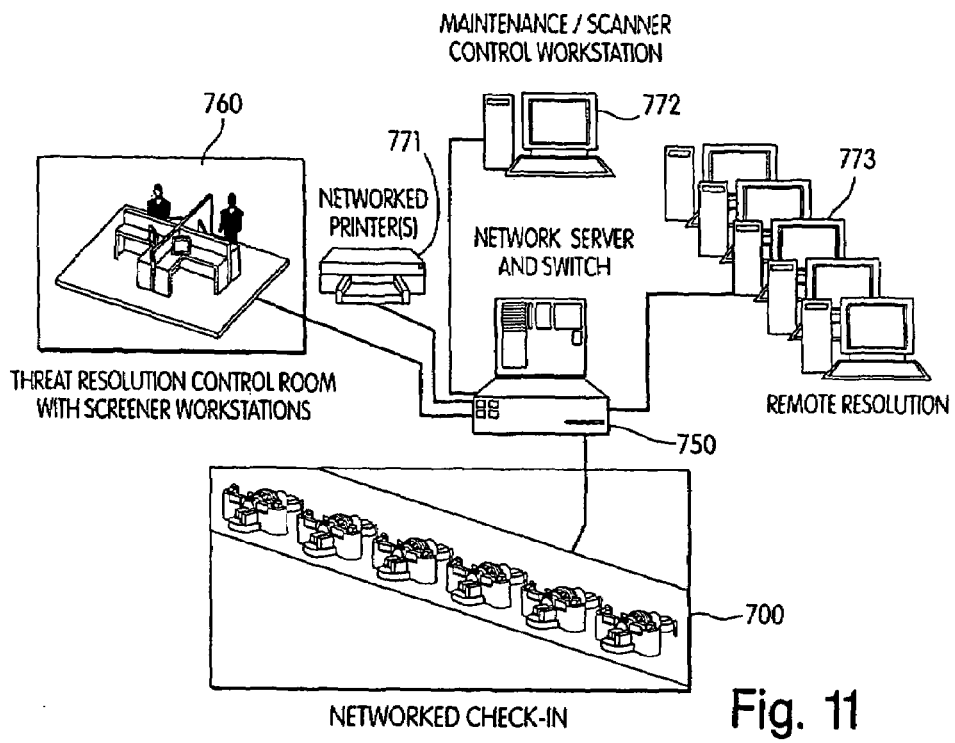
FIG. 11 is a block diagram of a networked CT scanner system according to an embodiment of the present invention.

The smaller size of the CT scanner of the present invention allows it to be more easily incorporated into the baggage handling process than existing EDS systems. FIG. 10 illustrates an airline check-in desk 700 incorporating a baggage scanner according to an embodiment of the present invention. As in some conventional check-in desks, the desk 700 of the present invention includes two check-in stations 710, 720 with a checked baggage loading area 730 between them. Multiple desks 700 could be positioned together in the airport lobby. The CT scanner 100 of the present invention is positioned at the baggage loading area 730. A passenger, upon checking in, places his or her baggage on the conveyor at the baggage loading area 730 or as a standalone system. The baggage is automatically scanned and processed for the existence of explosives. If the baggage passes, the check-in personnel can tag it in the ordinary manner and forward it to the baggage handling system. With the check-in desk of this embodiment of the present invention, very little additional lobby space is needed for scanning baggage, and no modifications to the baggage handling system are required. As an option, the bag can be processed as usual, with the bag tag placed by the ticket agent prior to scanning. Once checked-in, the bag is scanned and injected into the baggage handling system. If desired for improved operational flow, any suspect bag can be resolved in the baggage makeup area away from the passengers in the terminal area. Alternatively, the CT scanner of the present invention may be incorporated into a self service check-in desk, either as part of a check-in area of the lobby or as a free standing kiosk.

As described above, the CT scanner of the present invention may be a free standing, standalone unit with a TSA operator available for reviewing images and addreesing potential threats. According to another embodiment of the present invention, the host computers of a plurality of CT scanners 700 are networked together to form a single EDS. The networked CT scanners may include any combination of free standing units, self check-in units and integrated check-in desk units. Most bags can be automatically cleared by analysis of the scan data. However, some may require further review by an operator. Rather than have an operator at each scanner, as is used with carry-on baggage, a threat control room 760 with a plurality of operators is connected to the network. If a bag cannot be cleared automatically, the projection and/or reconstruction data is transferred to an operator in the threat control room 760. The operator can then determine whether a threat exists or can be cleared. If the possible threat is cleared by the operator, the bag is passed to the baggage handling system in the ordinary manner. However, if the threat cannot be cleared, the bag would be passed to other operators for a manual hand search. The network may include additional equipment, such as network server computers 750, printers 771, network control stations 772, and remote resolution computers 773.

The small size of the baggage scanning system also allows it to be placed in other locations for distributed handling of checked baggage. For example, a scanner could be placed for curb-side check-in or at rental car return areas for simplified processing. Additionally, hotels or other locations could provide check-in baggage service by providing a scanner and a secure area for scanned baggage. Guests could have their luggage automatically processed by the hotel and securely transferred to the airport without the need for further processing or delay during check-in. Additionally, the size of the scanner could permit it to be placed in a vehicle used to pick up baggage from various locations for transport to the airport. Free standing units can be provided at various locations in the airport for either self-checkin or assisted check-in of passengers. Alternatively, a CT scanner of the present invention may be used at security checkpoints for scanning of carry-on baggage. Each scanner, independent of its location in the airport or away from the airport, may be operated as a stand alone unit or may be networked for common review by TSA operators.

Figure 13:
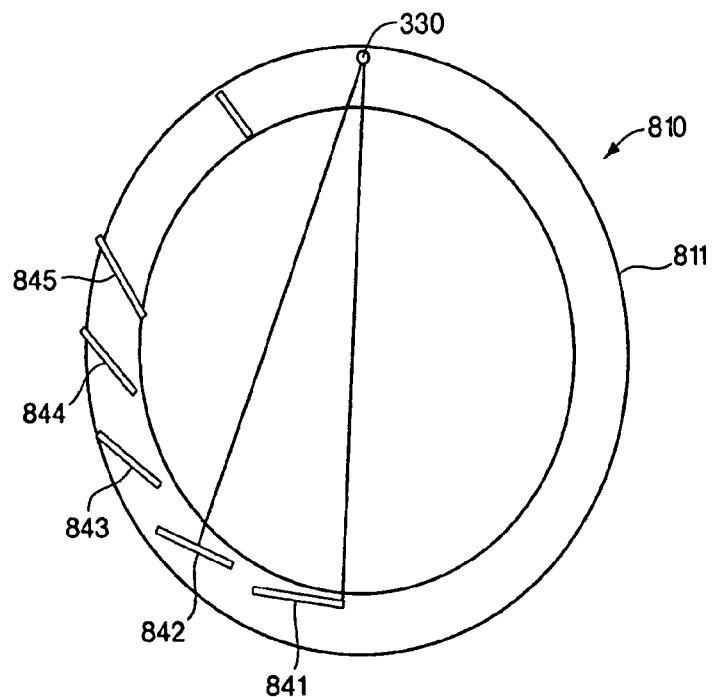
FIG. 13 is a cross sectional view of a CT scanner according to another embodiment of the present invention.
Figure 14C:
FIG. 14A–C represents data from the CT scanner of FIG. 13.
Figure 14B:
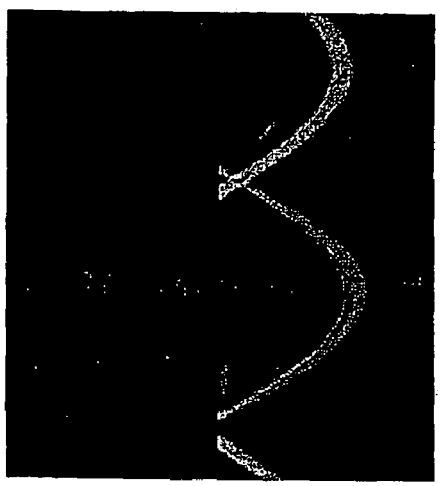
Figure 14A:
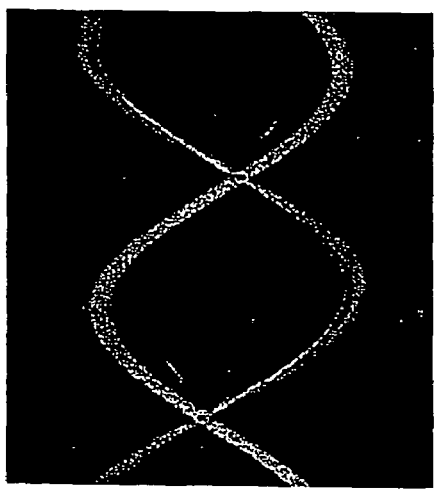

FIG. 13 illustrates another embodiment of the present invention which provides additional reductions in the size and cost. In the third embodiment, the CT scanner 810 has multiple detectors 841, 842, 843, 844, 845 located on half of the detector ring 811. As in the first two embodiments, the detectors are at different distances from the x-ray source 330 and at different angles. Using half a detector ring is sufficient for creating a CT reconstruction with a full 360 degrees of data. The half of a detector ring is mathematically equivalent to collecting data for 180 degrees plus fan beam, which is required for reconstruction. FIGS. 14A–14C illustrate CT reconstruction. FIG. 14A illustrates reconstruction using a full detector ring. FIG. 14B illustrates reconstruction of the same data from half a detector ring. The data from FIG. 14B can be used to complete a full reconstruction as illustrated in FIG. 14C. Using only half a detector ring, as in this embodiment, allows the imaging cost to be substantially reduced because fewer detectors are required.

In order to cut the cost further, the present invention may operate with reduced flux levels from conventional CT scanners. In the design of x-ray systems for baggage, one often designs the flux to be enough to penetrate the heaviest 5% of the bags. The majority of the bags require significantly less flux. By designing the system to provide flux for only the $90^{th}$ percentile bags, the amount of flux is significantly reduced. The reduced flux allows reduction in the noise levels and required shielding, which substantially reduces size and cost of the device. In order to handle the heavier bags, two or more scans are performed on the bags and the sinograms are averaged. The raw data can be analyzed, as discussed below, to determine which bags or regions of a bag are likely to require the extra flux. The bag slice gets scanned twice or more, averaging the second set of raw data with that obtained in the first rotation, which will reduce the noise in the reconstructed image and mimics a higher flux system. One can do this a 3rd or 4th time for those 1 thousandth bag slices of very heavily cluttered bags. The present invention reduces the need for manual bag searches by providing a practical solution to the "exceptional" or "shield" bag problem. Heavy or "shield" objects in unusual bags are scanned several times to obtain useful data with respect to heavily cluttered areas, without the need for a manual search.

Figure 15:
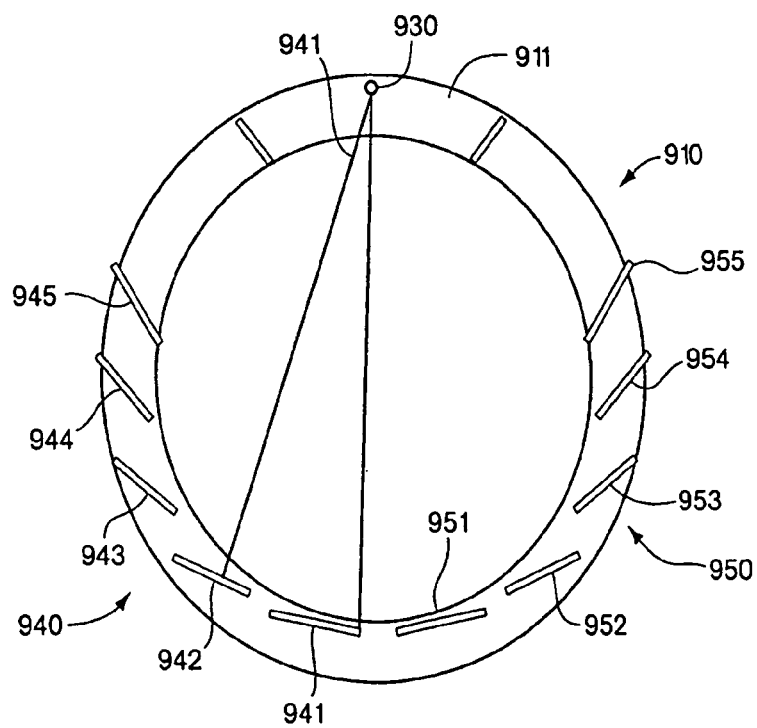
FIG. 15 is a cross sectional view of a CT scanner according to another embodiment of the present invention.

According to another embodiment of the present invention, the CT scanner of the present invention can be used for dual energy CT scans with a single pass of the baggage through the scanner. FIG. 15 illustrates a CT scanner 910 according to this embodiment of the invention. The CT scanner 910 includes a wide-angle x-ray source 930 and two sets of detectors 940, 950. Each of the sets of detectors 940, 950 includes a plurality of detector elements 941, 942, 943, 944, 945, 951, 952, 953, 954, 955. The detector elements for each set are each positioned on one half of the detector ring 911, as in the third embodiment. The two sets of detectors 940, 950 are sensitive to different energy spectrums. Using the CT scanner of this embodiment, two CT slices, of different energies, can be obtained from a single rotation of the detector ring. This will allow for a dual energy analysis of the CT images. One can also obtain dual energy CT images with back-to-back detectors. The dual energy CT is very useful to reduce the false alarm of the machine. This is very desirable in an airport environment. Although FIG. 15 illustrates five detector arrays for each set of detectors, any number of detector arrays may be used. Each set of detectors 940, 950, corresopnding to an energy level of the x-ray source, is positioned on one half of the detector ring 911.

The present invention has been described with respect to inspection of checked baggage, since it has substantial uses in that field. However, the reduced size of the folded array CT scanner according to the present invention can be used in many other applications for which CT scanners are used. For example, it may be used for cargo or pallette inspection or screening. A larger tunnel is typically necessary for cargo and pallette inspection, and conventional CT scanners are correspondingly much larger. The CT scanner of the present invention has a significantly smaller size, even with a large tunnel. The present invention may also be used in medical CT scanning applications.

Furthermore, the present invention has been described as including an x-ray source. Conventionally, CT scanners have used x-ray sources for radiation and appropriate detectors for x-rays. Of course, other radiation sources, such as gamma radiation, could also be used in connection with the present invention. With a different radiation source, the detectors and/or scintillator material would need to be changed as appropriate to measure the proper radiation spectrum.

Having described at least one embodiment of the invention, modifications, adaptations and improvements will be readily apparent to those of ordinary skill in the art. Such modification, changes and adaptations are considered part of the invention.

The invention claimed is:

1. A computed tomography (CT) scanner for scanning an object, the CT scanner comprising:
   a tunnel;
   a conveyor for moving the object through the tunnel;
   a gantry movable relative to the tunnel;
   an x-ray source for providing an x-ray beam that intersects the tunnel;
   a first set of detectors on the gantry, the detectors in the first set all being positioned substantially at a same first distance from the x-ray source, the first set of detectors being positioned opposite the x-ray source so that the gantry has first and second sections extending on opposite sides of the gantry between the x-ray source and the first set of detectors; and
   a second set of detectors positioned on the first section of the gantry, the detectors in the second set all being positioned substantially at a same second distance from the x-ray source, the second distance being less than the first distance.

2. The CT scanner of claim 1, further comprising a third set of detectors positioned on the second section of the gantry, the detectors in the third set all being positioned at substantially the second distance from the x-ray source.

3. The CT scanner of claim 1, wherein the x-ray source is a wide angle x-ray source.

4. The CT scanner of claim 1, wherein the first set of detectors is centered opposite the x-ray source.

5. An explosive detection system for screening airport passenger baggage, comprising:
   a computed tomography (CT) scanner comprising:
      a gantry movable relative to a tunnel;
      a wide-angle x-ray source; and
      a folded detector array, the folded detector array comprising;
         a first plurality of adjacent detectors, each of the detectors in the first plurality positioned at substantially a first distance from the x-ray source, the first plurality of adjacent detectors being positioned opposite the x-ray source so that the gantry has first and second sections extending on opposite sides of the gantry between the x-ray source and the first plurality of adjacent detectors, and
         a second plurality of adjacent detectors positioned on the first section of the gantry, each of the detectors in the second plurality positioned at substantially a second distance from the x-ray source, the second distance being different from the first distance.

* * * * *